(12) United States Patent
Pursley

(10) Patent No.: US 9,592,079 B1
(45) Date of Patent: Mar. 14, 2017

(54) DEVICE AND METHOD FOR ASSISTING REMOVAL OF ITEMS ENDOVASCULARLY

(71) Applicant: Matt D. Pursley, Dawsonville, GA (US)

(72) Inventor: Matt D. Pursley, Dawsonville, GA (US)

( * ) Notice: Subject to any disclaimer, the term of this patent is extended or adjusted under 35 U.S.C. 154(b) by 154 days.

(21) Appl. No.: 14/214,273

(22) Filed: Mar. 14, 2014

Related U.S. Application Data

(60) Provisional application No. 61/780,982, filed on Mar. 14, 2013.

(51) Int. Cl.
| | |
|---|---|
| *A61B 17/50* | (2006.01) |
| *A61B 17/00* | (2006.01) |
| *A61B 18/20* | (2006.01) |
| *A61F 2/01* | (2006.01) |

(52) U.S. Cl.
CPC ........ *A61B 17/50* (2013.01); *A61B 17/00234* (2013.01); *A61B 18/20* (2013.01); *A61F 2/01* (2013.01)

(58) Field of Classification Search
CPC .. A61B 17/320016; A61B 2017/00292; A61B 2017/00353; A61B 2017/00358; A61B 2017/00367; A61B 2017/32004; A61B 17/320783; A61B 2017/320791; A61B 18/1447; A61B 18/1442; A61B 2018/1452; A61B 2018/1455; A61B 17/0467; A61B 17/32; A61B 17/128; A61B 17/1285; A61F 2002/011
See application file for complete search history.

(56) References Cited

U.S. PATENT DOCUMENTS

| | | | | |
|---|---|---|---|---|
| 5,651,366 | A * | 7/1997 | Liang ................ | A61B 8/12 600/439 |
| 5,762,613 | A * | 6/1998 | Sutton ............... | A61B 10/06 600/564 |
| 6,328,730 | B1 * | 12/2001 | Harkrider, Jr. ..... | A61B 17/3421 600/130 |
| 7,651,503 | B1 * | 1/2010 | Coe ................. | A61B 17/320016 606/108 |
| 2004/0138685 | A1 * | 7/2004 | Clague ............. | A61B 17/12 606/167 |
| 2006/0095025 | A1 * | 5/2006 | Levine ............ | A61B 17/00234 606/15 |
| 2011/0105944 | A1 * | 5/2011 | Ohnishi ........... | A61B 10/0266 600/566 |

* cited by examiner

*Primary Examiner* — Lynsey Crandall
*Assistant Examiner* — Nathan A Baldwin
(74) *Attorney, Agent, or Firm* — Jeffrey L. Thompson; Thompson & Thompson, P.A.

(57) ABSTRACT

A device for assisting in the removal of items endovascularly includes a catheter, a cutting head, and a pull wire. The pull wire has a proximal portion protruding from a proximal end of the catheter and a distal end connected to the cutting head. The pull wire is movable within the catheter to selectively extend and retract the cutting head from the distal end of the catheter. The cutting head is arranged to hold and/or cut an item to be removed.

9 Claims, 3 Drawing Sheets

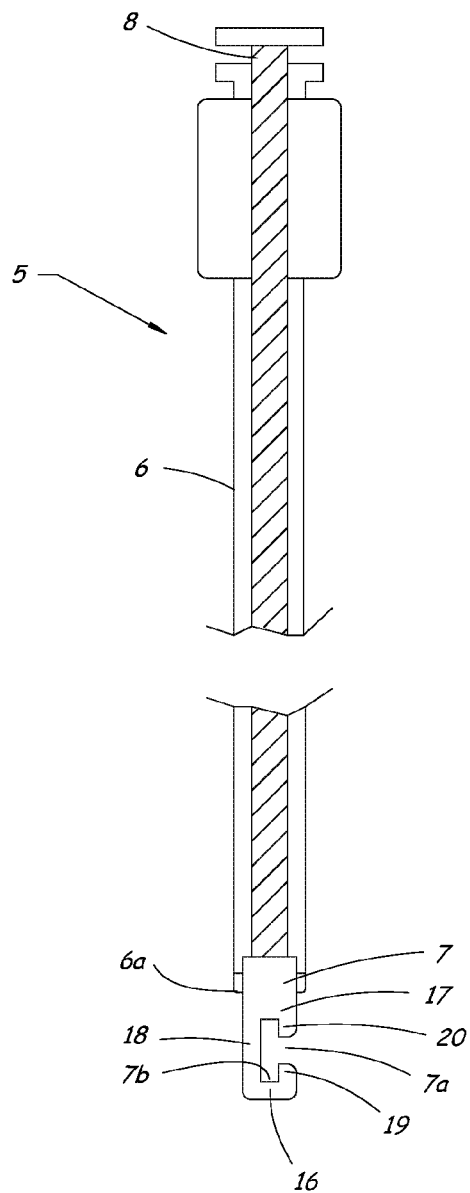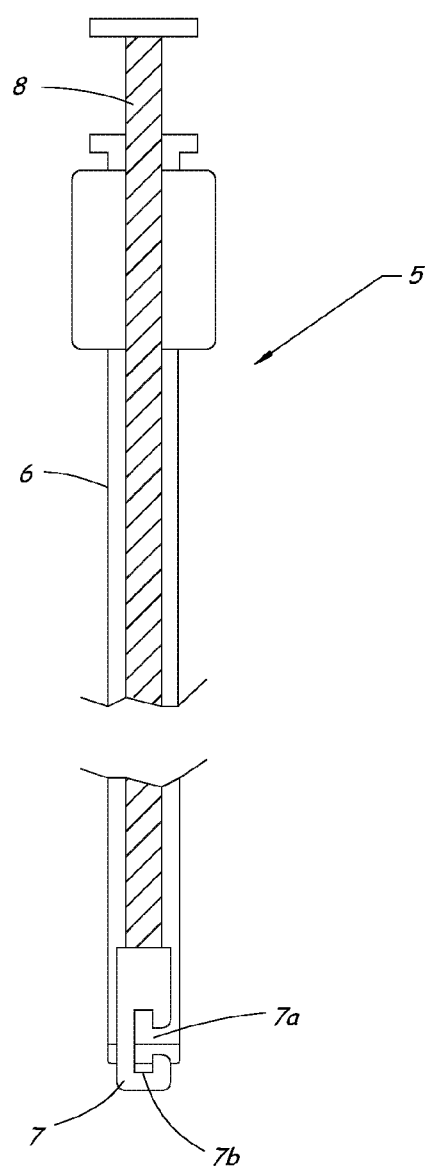

Fig. 3
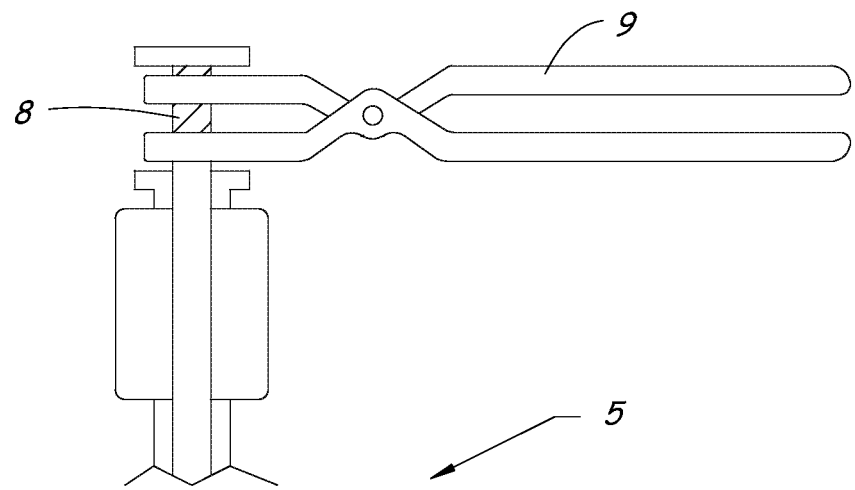
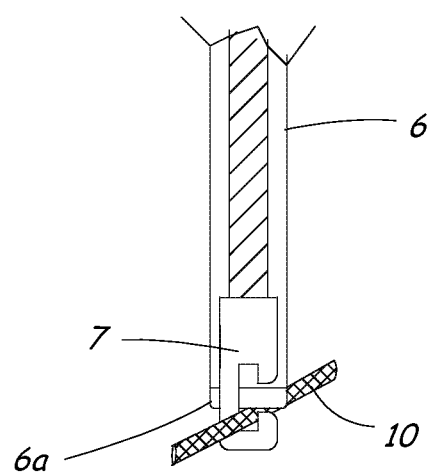

DEVICE AND METHOD FOR ASSISTING REMOVAL OF ITEMS ENDOVASCULARLY

RELATED APPLICATIONS

This application claims the benefit of U.S. Provisional Patent Application No. 61/780,982 filed on Mar. 14, 2013. The entire content of the priority application is incorporated herein by reference.

BACKGROUND OF THE INVENTION

Field of the Invention

The present invention relates generally to catheters, and in particular to catheters that can be used to assist in removal of items endovascularly.

Description of the Related Art

Inferior vena cava filters ("IVC filters") are medical devices that can be implanted into the inferior vena cava to prevent pulmonary emboli (PE). IVC filters are sometimes recommended for patients with contraindications to anticoagulation who either have acute PE or acute proximal (above the knee) deep vein thrombosis. IVC filters are normally placed by compressing them into a thin catheter, and inserting them via a blood vessel, such as the femoral vein, the internal jugular vein, or the arm veins. Once the distal end of the catheter reaches the IVC, the IVC filter is pushed through the catheter and deployed into the desired location.

IVC filters are typically attached to the vena cava by hooks on their ends. Some IVC filters are compression springs, which compress outward onto the sidewall of the vena cava; however, they still have small hooks that retain their location. These hooks aid in the anchoring and healing process, but they make it difficult to retrieve the IVC filter from the vena cava.

There is a need for a tool to assist with the removal of IVC filters after they have been deployed and to perform other endovascular cutting and removal operations.

SUMMARY OF THE INVENTION

It is an object of the present invention to provide a device and method for assisting in the cutting and/or removal of items endovascularly, including but not limited to the removal of IVC filters.

To accomplish these and other objects of the invention, a device according to the present invention for assisting in the removal of items endovascularly includes a catheter, a cutting head, and a pull wire. The pull wire has a proximal portion protruding from a proximal end of the catheter and a distal end connected to the cutting head. The pull wire is movable within the catheter to selectively extend and retract the cutting head from the distal end of the catheter. The cutting head is arranged to hold and/or cut an item to be removed.

According to one aspect of the present invention, a device for assisting in the removal of items endovascularly is provided, comprising: a catheter having a proximal end and a distal end; a cutting head; and a pull wire having a proximal portion protruding from the proximal end of the catheter and a distal end connected to the cutting head. The pull wire is movable within the catheter to selectively extend and retract the cutting head from the distal end of the catheter.

According to another aspect of the present invention, a method of removing items endovascularly is provided, comprising: providing a catheter having a proximal end and a distal end, a cutting head, and a pull wire having a proximal portion protruding from the proximal end of the catheter and a distal end connected to the cutting head; inserting the catheter into a vessel with the cutting head in a retracted position within the catheter; extending the cutting head from the distal end of the catheter; positioning the cutting head against an item to be removed; and retracting the cutting head into the distal end of the catheter to grasp and/or cut the item to be removed.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings:

FIG. 1 is an elevation view of a device for assisting removal of items endovascularly according to the present invention, with a cutting head in an extended position.

FIG. 2 is an elevation view of the device shown in FIG. 1, with the cutting head in a retracted position.

FIG. 3 is an elevation view of the device shown in FIGS. 1 and 2, with the cutting head being used to grip and/or cut an IVC filter strut and a cutter actuator at a proximal end for actuating the device.

DETAILED DESCRIPTION OF THE INVENTION

Figure 4:
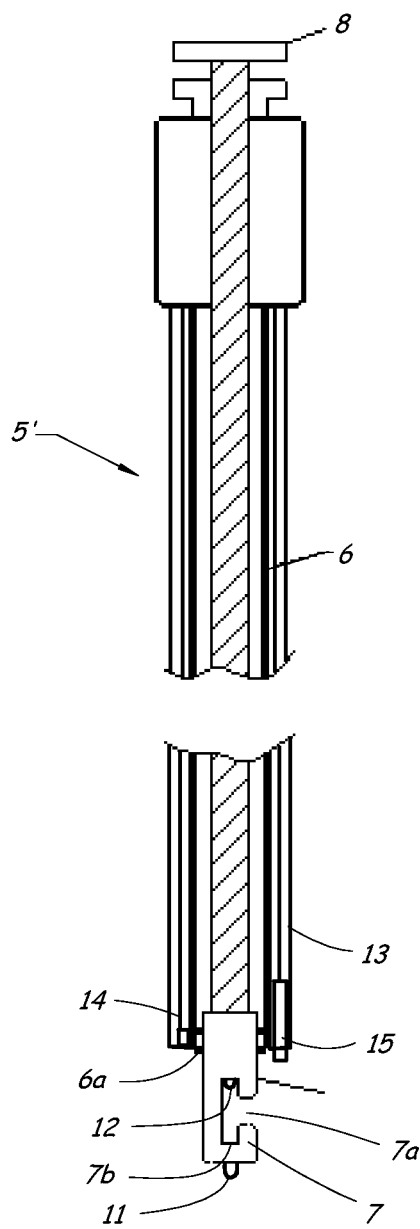
FIG. 4 is an elevation view of a modified device according to the present invention.

A device 5 for assisting removal of items endovascularly will be described in detail with reference to FIGS. 1 to 3 of the accompanying drawings.

The device 5 of the present invention can be used to assist in removal of items endovascularly, such as an IVC filter. As shown in FIG. 1, the device includes a catheter 6, a cutting head 7, and a pull wire 8 to actuate and/or retract the cutting head 7. The cutting head 7 can also be referred to as a holding/cutting head 7 because it serves a dual function of holding and cutting the items to be removed. The cutting head 7 has a generally C-shaped structure with an open lateral side 7a for receiving a portion of an item to be held or cut. The C-shaped structure has a distal portion 16 and a proximal portion 17 which are connected together by a connecting portion 18 that extends in a longitudinal direction between the distal portion 16 and the proximal portion 17 to form a closed lateral side of the C-shaped structure. The C-shaped structure also has a first projecting portion 19 that extends from the distal portion 16 toward the proximal portion 17, and a second projecting portion 20 that extends from the proximal portion 17 toward the distal portion 16. The open lateral side 7a is located between the first and second projecting portions 19, 20 on a side of the C-shaped structure opposite from the connecting portion 18. The distal portion 16 of the C-shaped structure has a sharpened inner edge 7b located between the connecting portion 18 and the first projecting portion 19, which faces in a proximal direction and functions to cut through an item when the item is held against the distal end 6a of the catheter 6 and a pulling force is applied to the pull wire 8. The device 5 is intended to give a physician the ability to enter a cavity, such as a vein, and make contact with and hold or cut an item, such as an IVC filter or an IVC filter strut 10.

As shown, the cutting head 7 can be retracted into the catheter 6 for deployment or removal. This prevents the cutting head 7 from snagging on things as it is deployed, removed or repositioned during a procedure. The device 5, with the cutting head 7 in its retracted position within the catheter 6, can easily be pushed past an item, such as an IVC filter. The cutting head 7 can then be extended from the distal end of the catheter 6. The physician can pull the cutting head 7 back as he positions it against the item to be removed until the cutting head 7 engages the item or portion of the item, such as an IVC filter strut 10. The cutting head 7 can then be partially retracted to grasp the item 10 as shown. Once the item 10 has been grasped, the physician can then use the catheter 6 to push/pull/rotate the item 10 and attempt to dislodge it.

If the physician is not able to dislodge the item 10, a cutter actuator 9 having a pair of pivoted jaws can be removably engaged to the proximal end of the catheter 6 and pull wire 8, as shown in FIG. 3. The actuator 9 can be used to increase the amount of force applied to the pull wire 8 to cause the cutting head 7 to cut the item 10, thereby freeing it. The cutting head 7 can then be retracted into the catheter 6 and repositioned to other items or portions of the same item that need assistance in freeing for removal.

Additional features can be added to the device 5 to expand its capabilities and better adapt the device for performing certain procedures. FIG. 4 illustrates a modified device 5' that includes an imaging system 11, a laser cutter 12, an additional lumen 13, and a second pull wire 14. The imaging system 11 can be, for example, an intravascular ultrasound probe incorporated into the cutting head 7 for imaging the vessels in which the device 5' is used. The laser cutter 12 can be incorporated into the cutting head 7 or the catheter 6 to further assist in cutting procedures. The additional lumen 13 can be added for inserting a balloon 15 or imaging catheter without interfering with the operation of the cutting head 7. The second pull wire 14 can be added to the catheter 6 for deflecting the catheter 6 during deployment to aid in attaching the cutting head 7 to the IVC filter strut 10.

While the invention has been specifically described in connection with a specific embodiment thereof, it is to be understood that this is by way of illustration and not of limitation, and the scope of the appended claims should be construed as broadly as the prior art will permit.

What is claimed is:

1. A device for assisting in the removal of items endovascularly, comprising:
   a catheter having a proximal end and a distal end;
   a cutting head; and
   a pull wire having a proximal portion protruding from the proximal end of the catheter and a distal end connected to the cutting head, said pull wire being movable within the catheter to selectively extend and retract the cutting head from the distal end of the catheter;
   wherein said cutting head comprises a generally C-shaped structure having an open lateral side for receiving a portion of an item to be held or cut; and
   wherein said C-shaped structure has a distal portion and a proximal portion which are connected together by a connecting portion that extends in a longitudinal direction between said distal portion and said proximal portion to form a closed lateral side of said C-shaped structure, said C-shaped structure further comprising a first projecting portion that extends from said distal portion toward said proximal portion, a second projecting portion that extends from said proximal portion toward said distal portion, and said open lateral side is located between said first and second projecting portions on a side of said C-shaped structure opposite from said connecting portion, and said distal portion of said C-shaped structure has a sharpened inner edge located between said connecting portion and said first projecting portion and facing in a proximal direction which is arranged to cut through an item when the item is held within the C-shaped structure against the distal end of the catheter and a pulling force is applied to the pull wire.

2. The device according to claim 1, further comprising an actuator having a pair of pivoted jaws removably engaged to the proximal end of the catheter and pull wire to increase an amount of pulling force applied to the pull wire during a cutting process.

3. The device according to claim 1, further comprising an intravascular ultrasound probe incorporated into the cutting head.

4. The device according to claim 1, further comprising a laser incorporated into the cutting head or catheter to assist in cutting.

5. The device according to claim 1, wherein said catheter comprises a first lumen for containing said pull wire and said cutting head, and a second lumen for inserting a balloon or imaging catheter.

6. The device according to claim 1, further comprising a second pull wire added to the catheter for deflecting the catheter to aid in attaching the cutting head to an item to be held or cut.

7. A method of removing items endovascularly, comprising:
   providing a catheter having a proximal end and a distal end, a cutting head, and a pull wire having a proximal portion protruding from the proximal end of the catheter and a distal end connected to the cutting head;
   said cutting head comprises a generally C-shaped structure having an open lateral side for receiving a portion of an item to be held or cut, said C-shaped structure has a distal portion and a proximal portion which are connected together by a connecting portion that extends in a longitudinal direction between said distal portion and said proximal portion to form a closed lateral side of said C-shaped structure, said C-shaped structure further comprising a first projecting portion that extends from said distal portion toward said proximal portion, a second projecting portion that extends from said proximal portion toward said distal portion, and said open lateral side is located between said first and second projecting portions on a side of said C-shaped structure opposite from said connecting portion, and said distal portion of said C-shaped structure has a sharpened inner edge located between said connecting portion and said first projecting portion and facing in a proximal direction which is arranged to cut through an item when the item is held within the C-shaped structure against the distal end of the catheter and a pulling force is applied to the pull wire;
   inserting the catheter into a vessel with the cutting head in a retracted position within the catheter;

extending the cutting head from the distal end of the catheter;

positioning the cutting head against an item to be removed with a portion of the item within said C-shaped structure; and retracting the cutting head into the distal end of the catheter to grasp and/or cut the item to be removed.

8. The method according to claim 7, further comprising retracting the cutting head to cause the sharpened inner edge to cut through the portion of the item positioned within said C-shaped structure.

9. The method according to claim 8, further comprising using an actuator having a pair of pivoted jaws removably engaged to the proximal end of the catheter and pull wire to increase an amount of pulling force applied to the pull wire when retracting the cutting head.

* * * * *